United States Patent [19]
Curran

[11] Patent Number: 4,939,933
[45] Date of Patent: Jul. 10, 1990

[54] ISOMETRIC STRENGTH TESTING METHOD AND EQUIPMENT FOR DISABILITY EVALUATION

[76] Inventor: Thomas M. Curran, 464 Springbrook, Saline, Mich. 48176

[21] Appl. No.: 409,250

[22] Filed: Sep. 19, 1989

Related U.S. Application Data

[62] Division of Ser. No. 92,432, Sep. 3, 1987, Pat. No. 4,882,677.

[51] Int. Cl.$^5$ ............................................. A61B 5/22
[52] U.S. Cl. .................................... 73/379; 272/68; 272/125
[58] Field of Search ................... 73/379; 272/68, 125, 272/DIG 5

[56] References Cited

U.S. PATENT DOCUMENTS

| | | | |
|---|---|---|---|
| 2,309,511 | 1/1943 | Kellogg | 73/379 |
| 3,442,132 | 5/1969 | DeMare | 73/379 |
| 3,752,144 | 8/1973 | Weigle, Jr. | 73/379 X |
| 4,805,455 | 2/1989 | DelGiorno et al. | 73/379 |

Primary Examiner—Charles A. Ruehl
Attorney, Agent, or Firm—James M. Deimen

[57] ABSTRACT

New disability testing and evaluation software combined with an isometric strength testing machine provides a very complete and standardized means of determining disability in comparison with the norms of the general population. The software utilizes not only the machine but also the digitization of photographs taken of the subject person during each strength test. Combining the digitized photographic data, the force monitor information from the load cell of the machine and extensive anthropomorphic data the software calculates for loading of the weakest joint in the subject person and compares this loading to normative values from the general population. In this manner a percentage disability for a subject person can be calculated with reasonable assurance of the validity and reproducibility of the result. New specialized hand grips for an isometric strength testing machine are disclosed to test grip strength and torsional strength of the hand.

17 Claims, 7 Drawing Sheets

```
TECHNICIAN: DR. JONES                                    DIRECTION
SUBJECT: JOHN SMITH
TASK #:1
JOB DESCRIPTION: LIFTING A BOX

PROFILE:
   AGE: 35
   SEX: M

BODY SIDE: R        EXERTION: 30 LBS
                    HANDS: 2
STATURE: A          DIRECTION: LIFT
HEIGHT: 72 IN.
WEIGHT: 167 LBS.

BODY ANGLES:
   ANKLE TO KNEE    : 85
   KNEE TO HIP      : 131
   HIP TO SHOULDER  : 13
   SHOULDER TO ELBOW : -90
   ELBOW TO HAND    : -68
DATE: 9-12-86
```

V = 15     H = 12

POPULATION % CAPABLE
(REFER TO WEAKEST LINK)

| ELBOW | SHOULDER | L5/S1 | HIP | KNEE | ANKLE |
|-------|----------|-------|------|------|-------|
| 99.9  | 99.9     | 99.1  | 90.5 | 99.8 | 99.2  |

BACK COMPRESSION: 950.7 LBS

FIG. 5

SUBJECT: JOHN SMITH
         VS. 75% OF POPULATION

TASK: LIFTING A BOX

SUBJECT LIMIT: ▨

EXPECTED LIMIT: ▢

FORCE

POPULATION % CAPABLE, WEAKEST LINK = HIP

ISOMETRIC STRENGTH TESTING METHOD AND EQUIPMENT FOR DISABILITY EVALUATION

This is a divisional of copending application(s) Ser. No. 092,432 filed on 09/03/87, U.S. Pat. No. 4,882,677.

BACKGROUND OF THE INVENTION

The field of the invention pertains to biomechanical strength testing of individual persons and, in particular, to the careful isometric strength testing of individuals disabled as a result of injuries. Strength testing relates to disability evaluations, pre-employment examination, job redesign and work conditioning.

In recent years, the importance of careful biomechanical modeling and the repeatability of results from strength testing to assure validity of the results has taken on great importance to assure that the physical labor required in a job is properly matched with the individual worker. More importantly, avoidance of injury and the proper evaluation of disabling injuries has become important not only because of the cost to the disabled but also the cost to society that also results.

Extensive research and careful analysis of the human body structure under physical stress is disclosed and summarized in a recent book by Don B. Chaffin, Ph.D. and Gunnar Anderson, M.D. entitled, "Occupational Biomechanics", 1984 John Wylie & Sons, Inc. The book presents extensive biomechanical guidelines and considerations for the physical work and workplace of an individual. On the bases of these guidelines and considerations, limits are suggested for various physical activities in various workplace situations.

A publication by the U.S. Department of Commerce, National Technical Information Service, sponsored by the U.S. Department of Health and Human Services, is entitled, "Work Practices Guide for Manual Lifting" and was published in Mar. of 1981 will reference number TB 82-178948. This technical report summarizes research on the hazards of manual materials handling in industry and recommends means to reduce the human and economic burden imposed by improper materials handling. Such recommendations include the safe load, weight, size, location and frequency of handling by a worker. Worker training and selection criteria are listed and engineering guidelines are provided for the design of the workplace.

At the University of Michigan in Ann Arbor, Mich., an isometric strength testing machine was developed with an electric sensor or load cell employed to sense the load applied to the machine by the subject individual. The purpose of the machine is for job analysis and employment screening and the electric sensor is directly connected to interface means to directly record the load applied to the machine by the subject. The machine and considerable supporting mainframe computer software was developed under a National Aeronautics and Space Administration supported contract. The principal publication arising from the research is Garg, A. and Chaffin, D. B., The Human Strength Simulations, Biomechanical Division NASA/MSC Contract #NAS9-10973, Apr. 1972.

The machine comprises a vertical assembly post and a horizontal platform. At various heights on the vertical assembly post, a horizontal arm may be positioned. The horizontal arm contains the necessary sensor and a single or double hand grip for the subject to apply a load to the machine. Depending on the height of the hand grip, the subject may be in various postures, such as partially bent over to lift a load from the platform, pushing against the hand grip, or raising a load over the subject's head. As a result of the development of the machine and the mainframe software, considerable research was accomplished in job analysis and employment screening.

SUMMARY OF THE INVENTION

The invention comprises new specialized hand grips for the testing machine and new software combined with the machine specifically directed toward disability evaluation of subjects. The disability evaluation software utilizes not only the testing machine but also the digitization of photographs of the subject taken in each isometric position as the subject is performing the load test on the machine. The new software combines the digitized information taken from the photographs and the information from the load cell or sensor of the machine along with other information about the subject. The software calculates from this information a number of body dimensions and angles, certain loads and weights that are critical to disability evaluation and the percentage capabilities of various body joints relative to the capability of a large percentage of the general population. The new combination of software and hardware allows the technician to evaluate a subject by having the subject perform the simulated lifting of a load from the platform by isometrically attempting to lift the load over three separate five second intervals. The photographs are taken as the subject is exerting maximum force on the hand grip of the machine. At the same time, the load on the machine is being recorded on a strip chart which typically results in a somewhat bell-shaped curve over each five second time period. The data from the photographs and the strip chart recorder may then be immediately digitized and processed by the disability software or processed subsequently.

For the lifting of a load from the platform, a "tote pan" simple hand grip on the testing machine may be used. The hand grip may be raised to higher positions including an overhead position on the machine. However, two new specialized hand grips have been developed for use in combination with the machine. The first of the new grips provides a simple hand squeezing motion wherein the squeezing motion is strictly limited to sliding motion of the grip. A purely tensile load is placed on the grip by the hand and the grip is insensitive to right-side-up or upside-down placement of the hand. The other new grip comprises a torque sensing attachment. The torque sensing attachment, depending on hand placement and movement, senses flexion/extension torque, pronation/supination torque, and ulnar/radial deviation torque. With each test, the instantaneous load sensed by the testing unit is printed out on a strip chart recorder and the test repeated.

One of the important advantages of the new test methods, software analysis and specialized hand grips is that with repeated testing such as three repeated tests for each load position prescribed, a very confident prediction of the percent disability of the subject in comparison with satistical norms developed from the general population results. Any attempted malingering by the subject also faults the test or appears clearly in the test results.

Description of the Preferred Embodiments

Figure 1:
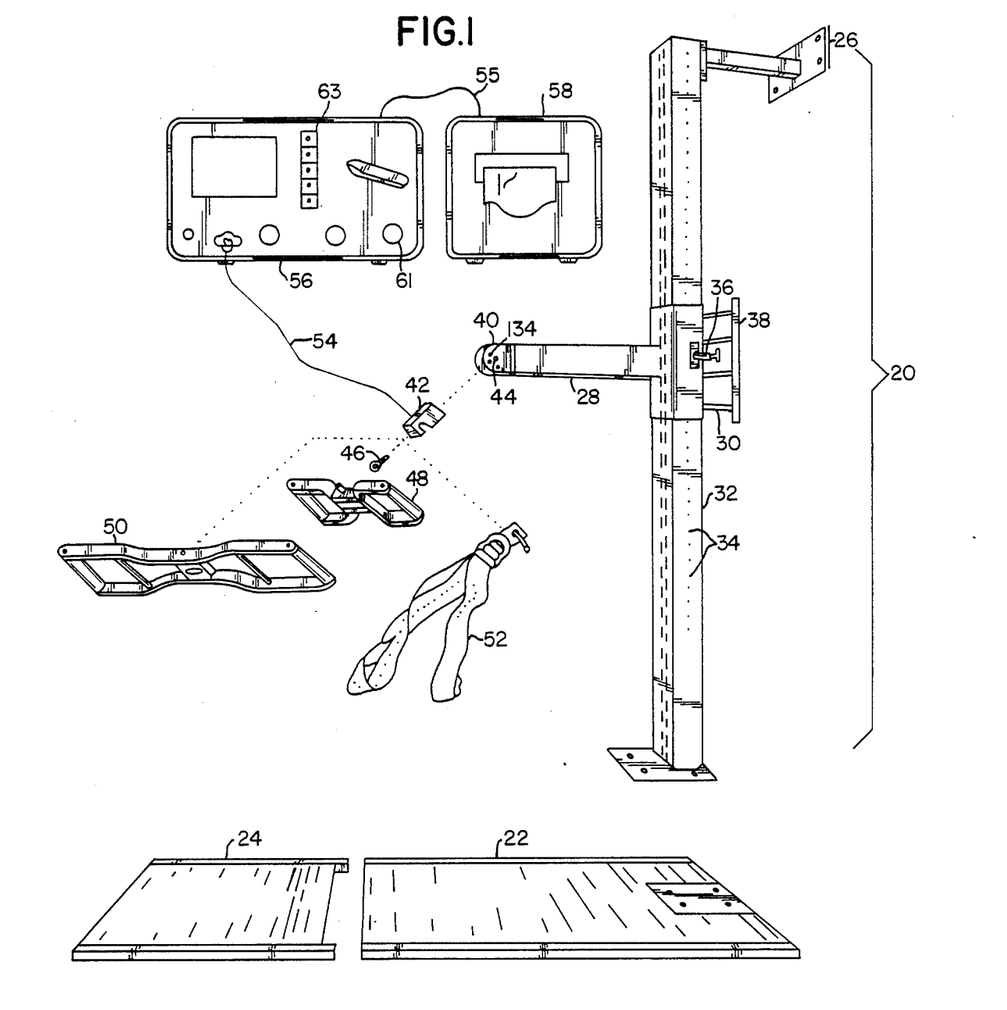
FIG. 1 illustrates an exploded view of the basic platform and vertical assembly plus electronics of the testing machine.

Illustrated in FIG. 1, in exploded view, is a vertical post assembly 20 that attaches to a platform 22 having an extension 24. Atop the vertical post assembly is an optional bracket 26 to attach the post to a wall if the platform is not used. Movable vertically to selectable positions is a horizontal arm 28 having a sleeve 30 about the post 32. The post 32 is provided with holes 34 engageable by a pin 36 with which to select and retain the vertical position desired. The sleeve 30 is also equipped with means 38 movable to squeeze the sleeve tightly to the post and thereby reduce compliance. The horizontal arm 28 is equipped with a head 40 having a load cell 42 that may be rotatably positioned in five separate angular locations relative to the arm 28 about the pivot point 44.

Selectively attachable to the load cell 42 by means of an eye-bolt 46 are a small double handle 48, a large double handle 50 and a parachute strap 52. A subject person standing on the platform 22 may present a variety of isometric loads to the machine depending upon the vertical position of the arm 28, the angular position of the load cell 42 and the particular handle or other attachment to the load cell. For example, the arm may be placed at approximately the hip height of the subject and the parachute strap 52 attached about the hips of the subject. With the subject straining away from the arm 28, an isometric load may be placed on the load cell 42 to simulate the towing or dragging of a load with a strap. Or, the small set of handles 48 attached to the load cell 42 and the arm 28 at approximately chest height of the subject can be used to simulate the pushing of a large load. As a further example, the arm 28 may be positioned at approximately knee height or below with the large handle 50 attached to the load cell 42 and the load cell 42 in the upward vertical position. This configuration simulates the initial lifting load of a tote pan or other similar object. Electrically connected 54 to the load cell 42 is a force monitor 56. In turn electrically connected 55 to the force monitor 56 is a strip chart recorder 58. The force monitor 56 includes test and reset positions on a selectable switch 61 to assure that once the individual test of the subject begins, the subject applies the load to the full extent of his ability for the full five second test period in the examples given below without interruption. Simultaneously, the strip chart recorder 58 plots the load versus time. The test position of the force monitor includes a threshhold setting. If the test subject lets up during the last three seconds of the five second test, a red light 63 signals and the test is voided.

Figure 11:
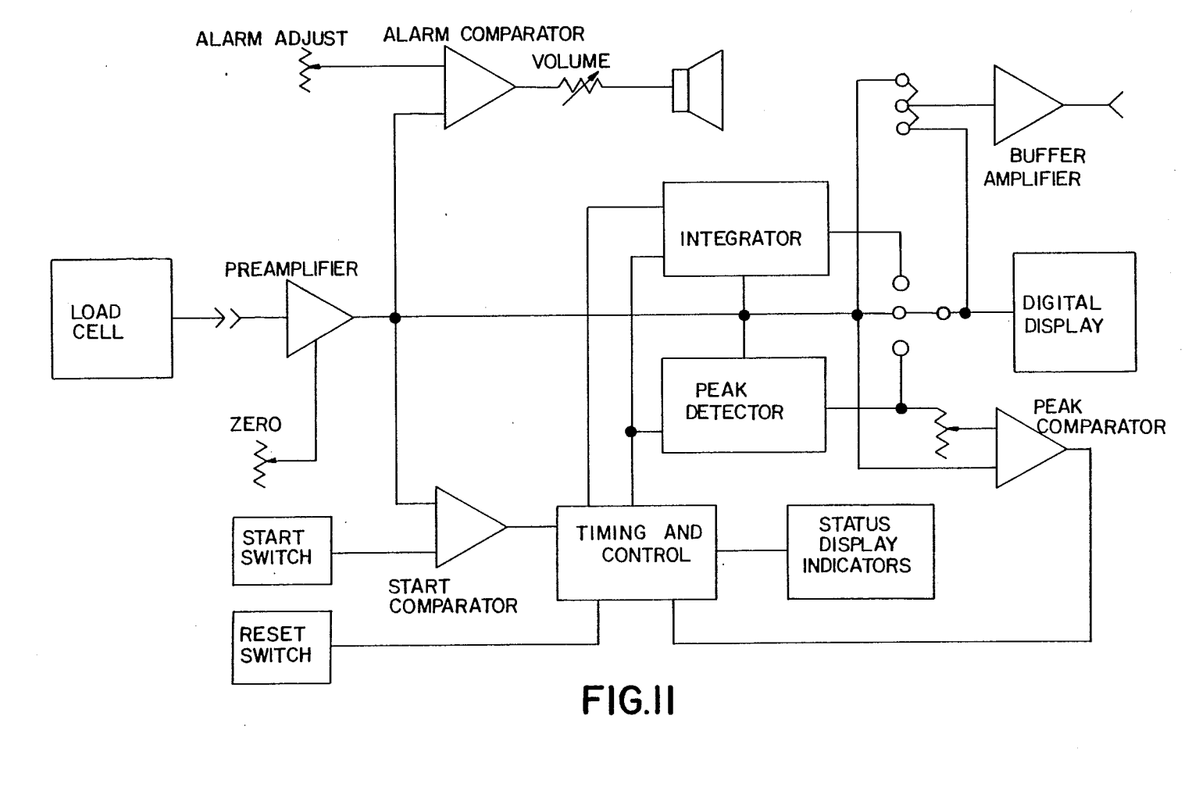
FIG. 11 is a detailed block diagram of the force monitor.

A suitable strip chart recorder 58 is the unit from BBC Metrawatt, Bloomfield, Colo. The force monitor 56 is a signal conditioning and digital display unit for analysis of the forces applied to the load cell 42. The force monitor 56 includes a load cell exitation source, tracking peak detector, gated averaging circuitry, timing and error detecting circuits. Although separate electronic devices can be combined to provide these functions, the force monitor provides an easy to use single unit that can be quickly reset for each test and gives both an audible and visual error signal if a force above a selectable threshhold is not maintained for the full test period. A detailed block diagram of the force monitor 56 is illustrated in FIG. 11.

A basic overall evaluation of a subject person can be obtained by analysis of the results of three isometric tests with the 6 inch handles 48 or 18 inch handles 50. Each test comprises a lift simulation with the arm 28 at the appropriate height on the vertical post 32. For the arm lift the elbows are close to the body and at right angles. Thus, the arm 28 is adjusted in accordance with the stature of the person. For the torso lift and leg lift the vertical height of the hand grips on the hanlde 50 is 15 inches. For the torso lift the person is placed with the upright torso horizontally 10 inches from the centers of the hands on the handle 50 and for the leg lift the upright torso is even horizontally with the centers of the hands on the handle 48.

Each test is repeated three times to assure repeatibility and the following measurements recorded:

(a) body stature and type of lift.
(b) body angles measured from photographs taken from the side during maximum effort.
(c) average peak forces and peak forces.
(d) force curves.

A comparison is then made against statistical norms derived from the biomechanical modelling the references noted above. In the disability setting a disability is considered less than 75% performance in comparison to normative maximum values of what a healthy person can accomplish. For the average healthy person 40% of the normative maximum value is considered the repetitive maximum for work in an 8 hour day. For repetitive all day manual lifting the limits considered are 35 lbs. for the average male and 20 lbs. for the average female.

The new disability testing software is specifically directed to analysis of the isometric strength of a subject person engaged in a single task. The task comprises attempting to lift a "tote bin" from the floor and is simulated by positioning the large 18 inch double handle 50 on the head 40 of the arm 28 such that the hand grips are horizontal. The load cell 42 is thus vertical in the head 40. For the test the arm 28 is positioned vertically on the post 32 to place the hand centers 15 inches above the platform. The subject person is placed with the upright torso about 10 inches horizontally from the centers of the hands.

Figure 2:
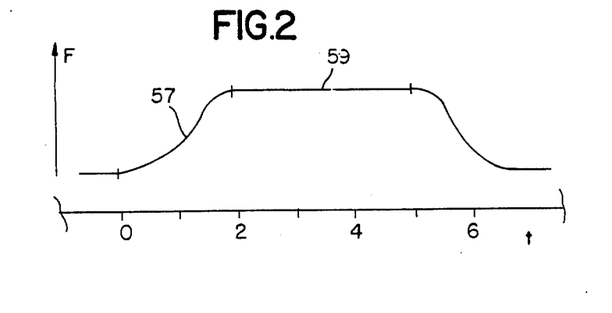
FIG. 2 is a force versus time graph of a test.

The subject person is requested to pull upwardly with both hands on the hand grips with maximum effort for a five second interval during which time a picture from the side is taken on the person. The test is repeated three times with a rest interval of at least two minutes in between. The force monitor 56 is reset between each test and the strip chart recorder 58 prints a curve of force versus time for each test. The curve of force versus time is bell shaped as illustrated in FIG. 2 with the rise time 57 typically about two seconds and hold time 59 the remaining three seconds of the five second test. In the event the subject person relaxes or lets up during the three second maximum force period an error light appears on the force monitor 56. A threshhold force is also set on the force monitor 56 prior to initiation of the test. Thus, malingering will be detected.

Figure 3A:
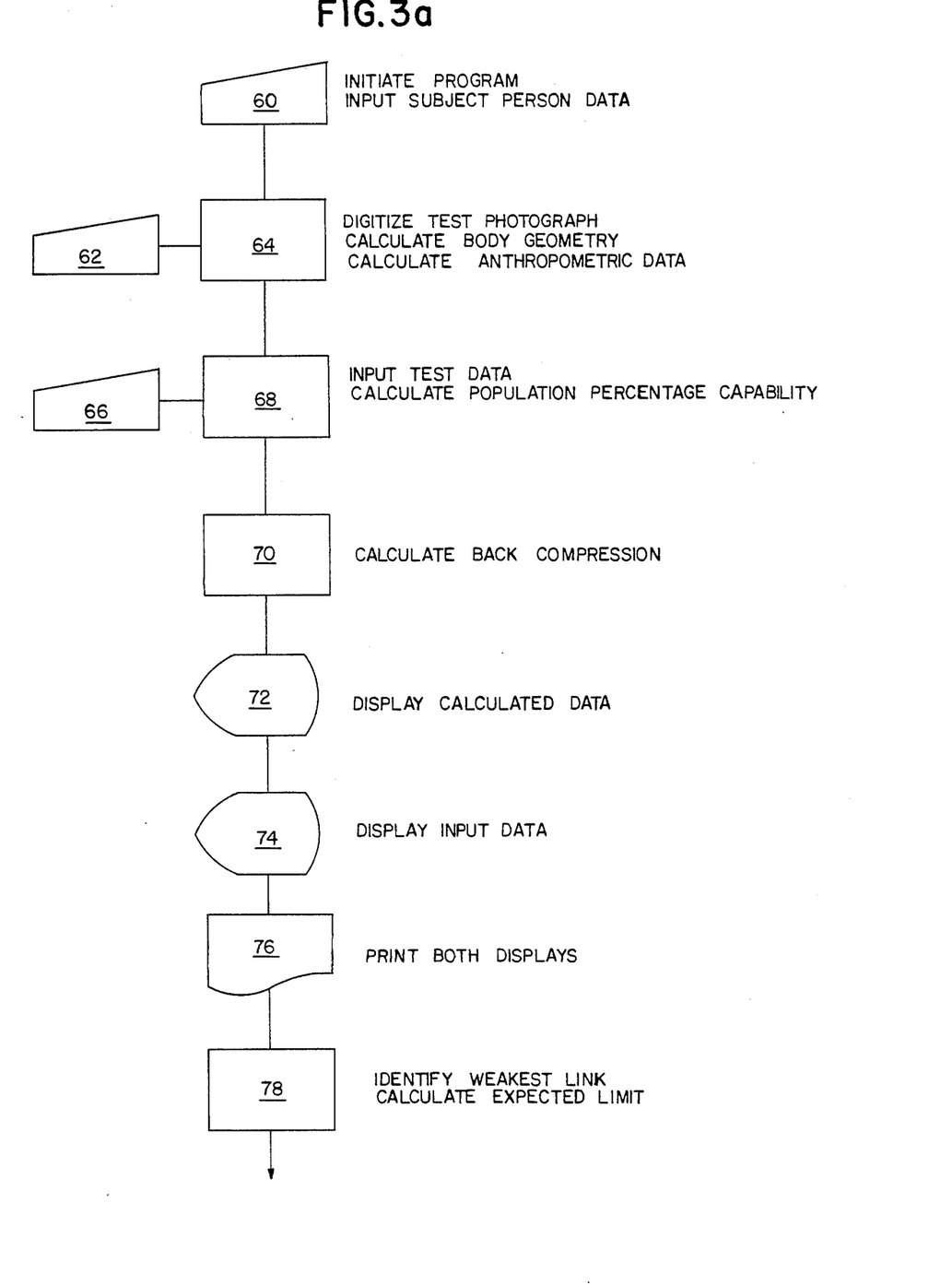
FIGS. 3a and 3b illustrate a biomechanical model flow chart for the software.
Figure 3B:
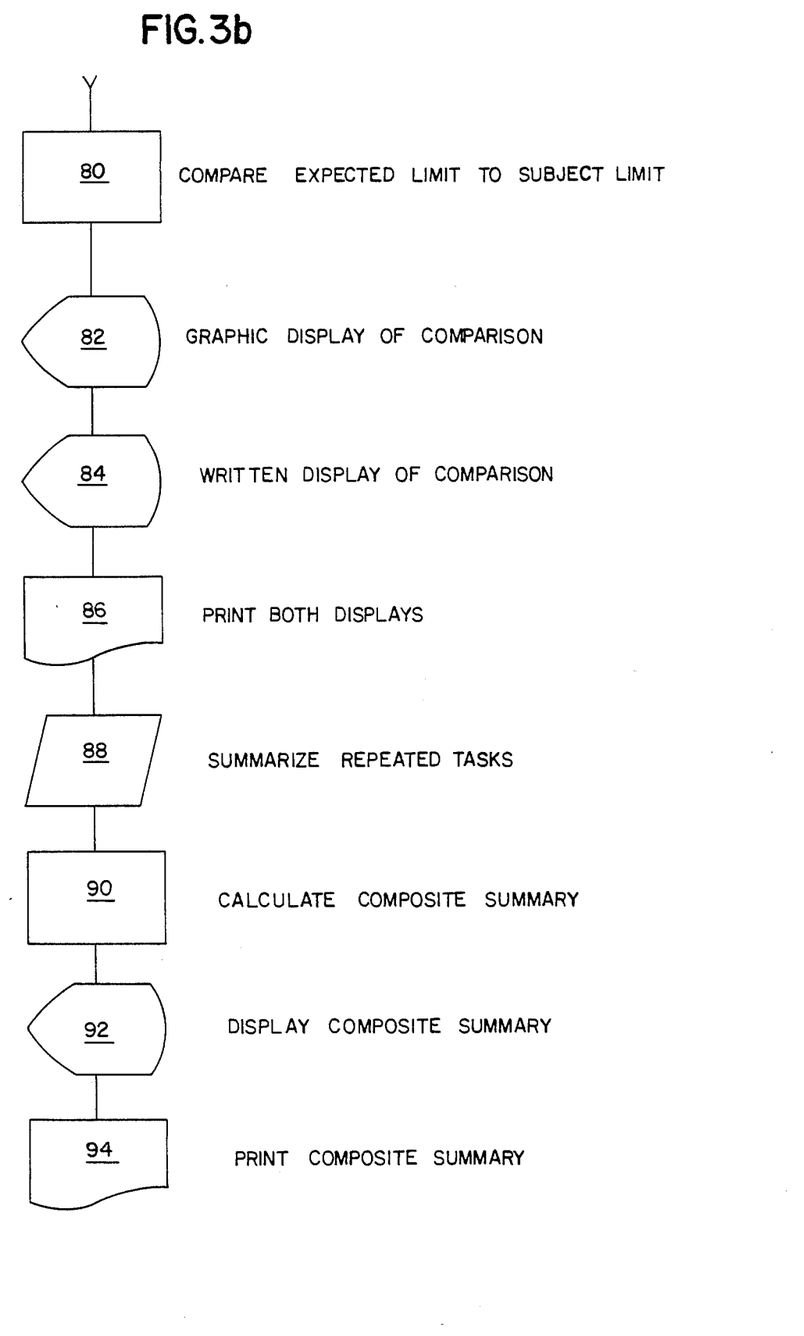

Illustrated in FIGS. 3a and 3b is a biomechanical model flow chart for the software utilized to prepare the "tote bin" isometric test results.

Block 60 denotes the entry of the following subject person data:
  English or Metric ?
  Current date.
  Technician.
  Subject.
  Task #.
  Age.
  Sex.
  Body side (photograph side).
  Height.
  Weight.

Block 62 denotes digitization of the subject's test photograph and calculation of body geometry including pertinent angles. A Polaroid photograph is suitable with a digitizer from Numonics Corporation, Montgomeryville, Pa.

Block 64 denotes calculation of the anthropometric data using the formulae and approach disclosed in "Occupational Biomechanics", Chapter 3.

Block 66 denotes the entry of the following testing data:
  Number of hands.
  Direction of motion.
  Average peak exertion from force monitor.
  Horizontal distance (H).
  Vertical distance (V).

Block 68 denotes calculation of the population percentage capability using the approach and formulae disclosed in "Occupational Biomechanics", Chapter 6.

Block 70 denotes calculation of back compression using the formulae and approach in "Occupational Biomechanics", Chapter 6.

Figure 4:
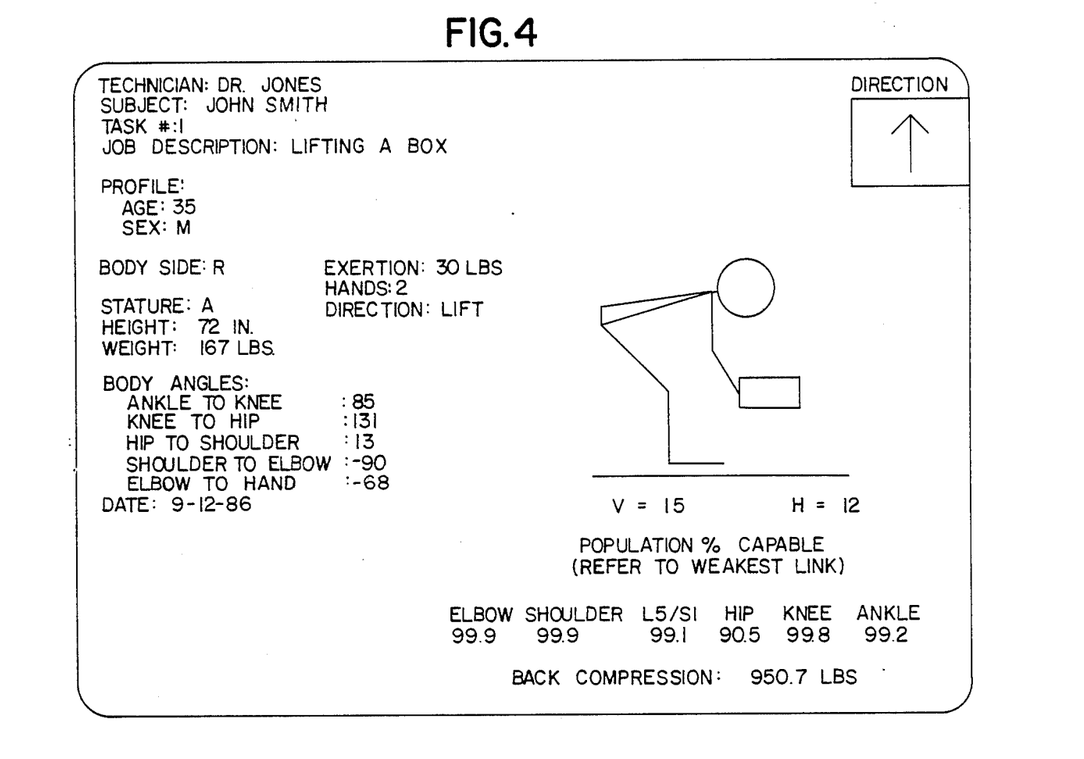
FIG. 4 illustrates an example of the output screen showing the results of the digitization of a photograph and the load calculations.

Blocks 72 and 74 denote screen display of the calculated data and input data entered in the form of a chart as shown in FIG. 4 and a table as follows in a typical example. In the table the figure and page references are to "Occupational Biomechanics".

TABLE 1

14/30 Ergometrics Biomechanical Model
Analyst: DR. JONES          Age: 35
Subject: JOHN SMITH         Sex: M
Task: LIFTING A BOX
Height:              72
Weight:              167
Ankle to Knee:       85
Knee to Hip:         131
Hip to Shoulder:     13
Shoulder to Elbow:   −90
Elbow to Hand:       −68
Direction:           270
Weight:              30
No. Hands:           2

| | FIG. 3.8, Page 69 | FIG. 3.9, Page 73 | Table 3.11, Page 72 |
|---|---|---|---|
| Body Link | Length (Cm) | Center of Gravity (Cm) | Weight (N) |
| Elbow | 44.99 | 25.51 | 34.15 |
| Shoulder | 44.81 | 25.40 | 77.58 |
| L5/S1 | 9.88 | 4.94 | 141.89 |
| Hip | 40.60 | 36.13 | 269.38 |
| Knee | 34.02 | 14.83 | 23.01 |
| Ankle | 35.48 | 15.26 | 18.93 |

| Calc. From Input Angles | | Page 224 | Page 224 | Page 224 | Page 224 |
|---|---|---|---|---|---|
| Body Link | Included Angle | Flexion | S.D. | Extension | S.D. |
| Elbow | 85.00 | 0.00 | 0.00 | 146.29 | 48.38 |
| Shoulder | 134.00 | 108.43 | 31.81 | 166.35 | 58.27 |
| L5/S1 | 62.00 | 113.00 | 30.84 | 248.34 | 99.73 |
| Hip | 125.21 | 47.85 | 14.06 | 811.79 | 255.88 |
| Knee | 77.00 | 86.74 | 20.05 | 97.62 | 30.58 |
| Ankle | 158.00 | 63.41 | 15.58 | 29.89 | 6.02 |

| | Page 165 Vertical Resultant | | Page 165 Horizontal Resultant | | Total |
|---|---|---|---|---|---|
| Body Link | Force [N] | Moment [NM] | Force [N] | Moment [NM] | Moment [NM] |
| Elbow | −425.98 | −28.02 | −0.00 | 0.00 | −28.02 |
| Shoulder | −391.83 | −11.90 | −0.00 | −0.00 | −11.90 |
| L5/S1 | −314.25 | −117.20 | −0.00 | −0.00 | −117.20 |
| Hip | −486.62 | −205.15 | −0.00 | −0.00 | −205.15 |
| Knee | −108.62 | −9.94 | −0.00 | −0.00 | −9.94 |
| Ankle | −85.61 | −9.94 | −0.00 | −0.00 | −9.94 |

| | | |
|---|---|---|
| Pelvic Angle From Vertical: | 32.1 | Page 192 |
| Angle Alpha From Horizontal: | 17.9 | Page 193 |
| Weight above L5/S1: | 269.4 | Page 72 |
| Diaphragm Moment Arm: | 14.7 Cm | Pages 194–195 |
| Abdominal Press: | 0.00 N/Cm 2 | Page 196 |
| Abdominal Force: | 5.9 N | Page 197 |
| Erector Spinae Muscle Force: | 4085.5 N | Page 197 |

TABLE 1-continued

| | | |
|---|---|---|
| Rectus Abdominus Muscle Force: | 0.0 N | Page 197 |
| Lumbodorso Fascia Strain: | 0.0% | Page 197 |
| L5/S1 Compression: | 4229.2 N | Page 199 |

Both screen displays may be printed for a permanent record as indicated at block 76.

Block 78 denotes identification of the weakest link (Hip in example) and calculation of the expected limit for the weakest link equal to 75% by increasing or decreasing the exertion to obtain the 75%. If rotation is involved enter the degree of rotation and adjust expected limit by 10%, 15% or 30% for 30.,60. or 90. rotation respectively.

Figure 5:
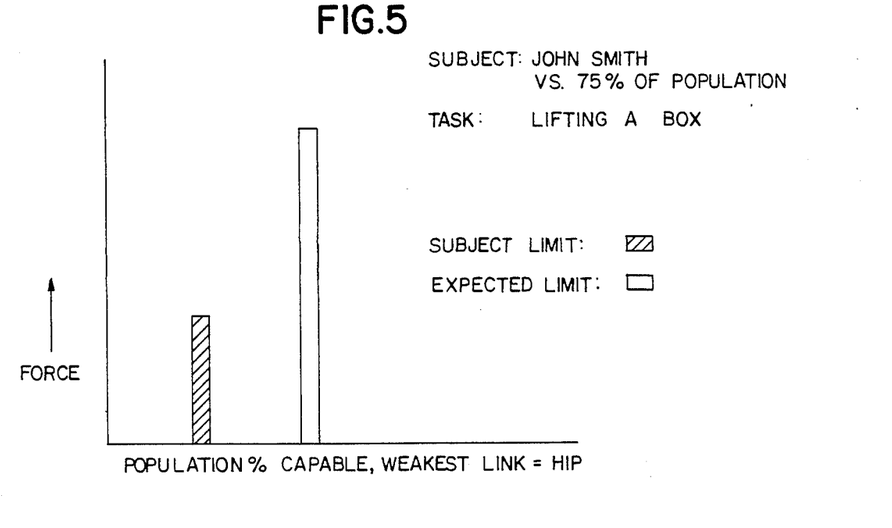
FIG. 5 is a subject comparison chart.

Block 80 denotes comparison of the subject's expected limit to the subject's exertion which is then screen displayed graphically as indicated by Block 82 and in written format by Block 84. Examples are illustrated by FIG. 5 and the following format:

---
Date: 9-12-86
Task #: 1
Description: LIFTING A BOX
---
Task #1 involved an isometric lift, vertical (V) 15 inches from the floor and horizontal (H) 12 inches from the midline of the body. The subject was able to exert a force that would be equal to lifting and holding 30 lbs. in this posture.

| | |
|---|---|
| Subjects exertion: | 30 lbs. |
| Expected limit: | 78 lbs. |
| Weakest link: | Hip |
| Score: | 38% |

Block 86 denotes printing of the screen displays in Blocks 82 and 84.

Block 88 denotes the summary of the three repeated tasks in terms of task number, exertion and expected limit. A final composite summary is denoted by Block 90 and calculated as follows:
A. The exertions are averaged.
B. The expected limits are averaged.
C. The average exertions are divided by the average expected limit.
D. The percent strength impairment is calculated:
  1. If average exertions are greater than average expected limits then no apparent impairment.
  2. Otherwise subtract the percentage result from "C" from 95% to determine the strength impairment.
E. The percentage result from "C" is multiplied by 35 lbs. and 20 lbs. to calculate male and female weight restrictions.

Block 92 denotes screen display and Block 94 printing of the summary as shown in the following example format:

SUMMARY

A. Total Exertions 155 Lbs./Number of Tasks 5=31
B. Total Expected Limits 388 Lbs./Number of Tasks 5=78
C. Score (A/B)=39.95%
D. Percent of Strength Impairment=55.05%
E. Weight Restriction=14 Lbs. for Males 8 Lbs. for Females As an option the philosophy of the biomechanical model employed and the isometric strength testing unit may be printed as an attachment to the printouts above. The software employed has been written in Turbo Pascal for the disability evaluation and employed on an IBM PC 2 Model 30 with an Epson Model EX 800 printer.

Figure 6:
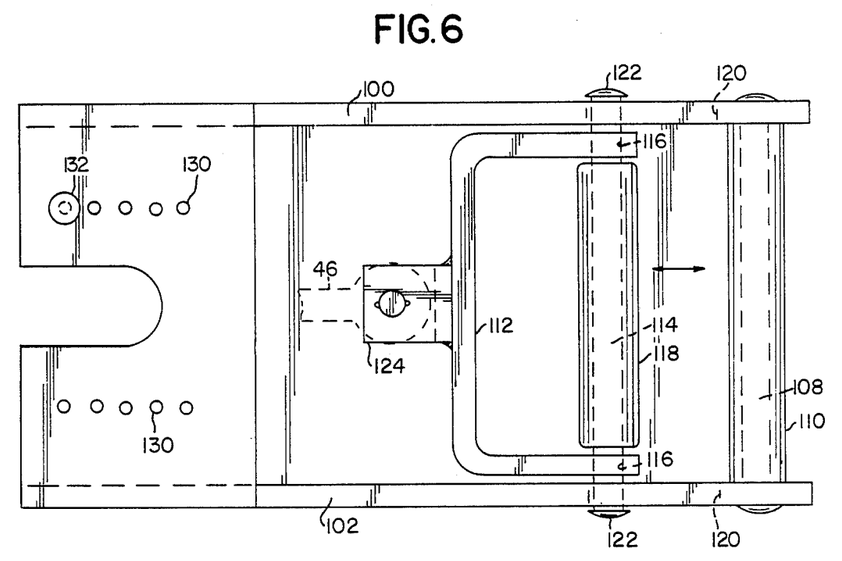
FIG. 6 is a side view of the new squeeze grip attachment.
Figure 7:
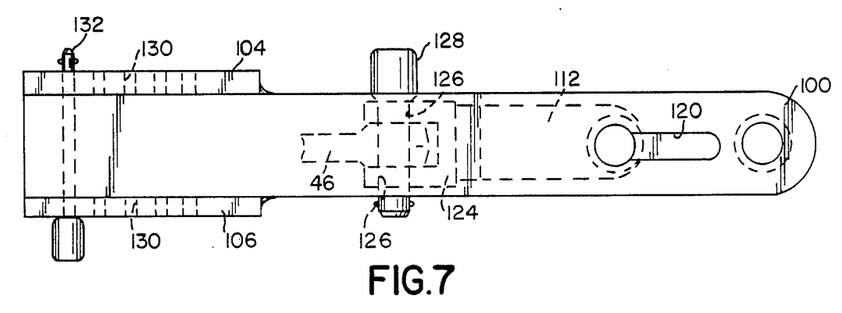
FIG. 7 is a top view of the new squeeze grip attachment.

In FIGS. 6 and 7 the new squeeze grip attachment is illustrated. The new squeeze grip comprises upper 100 and lower 102 frame members and a pair of side plates 104 and 106 that join the frame members together permanently. At the opposite end of the attachment is a frame bar 108 permanently joining the upper 100 and lower 102 frame members together. Frame bar 108 is covered with a relatively soft foam grip material 110.

Between the upper 100 and lower 102 frame members is a movable handle 112 having a handle bar 114 extending vertically through holes 116 in the bifurcated end of the handle. The handle bar 114 is also covered with a soft foam grip material 118 between the bifurcated ends. Beyond the holes 116 the handle bar 114 extends through a pair of slots 120 in the upper 100 and lower 102 frame members. Fasteners 122 assure that the handle bar 114 remains properly positioned as it is slid toward and away from the frame bar 108.

At the center of the handle 112 is a bifurcated bracket 124 bored horizontally 126 to accept a removable pin 128 for attachment to the eye-bolt 46 and load cell 42 of the horizontal arm 28 (see FIG. 1). Side plates 104 and 106 include a plurality of horizontally aligned sets of holes 130. Removable pins 132 selectably engage the holes 130 and matching holes 134 in the head 40 above and below the head pivot point 44. The particular set of holes 130 selected determine the neutral or unloaded position of the handle 112 and handle bar 114. Thus, the squeeze grip can be adjusted for hand size. In combination with the vertical post assembly and complete unit shown in FIG. 1, the squeeze grip can be set at the proper elevation. The sliding motion of the squeeze grip provides a pure measure of tension on the load cell 42 without torque thus, the hand may be right side up or upside down in placement on the grip.

Figure 8:
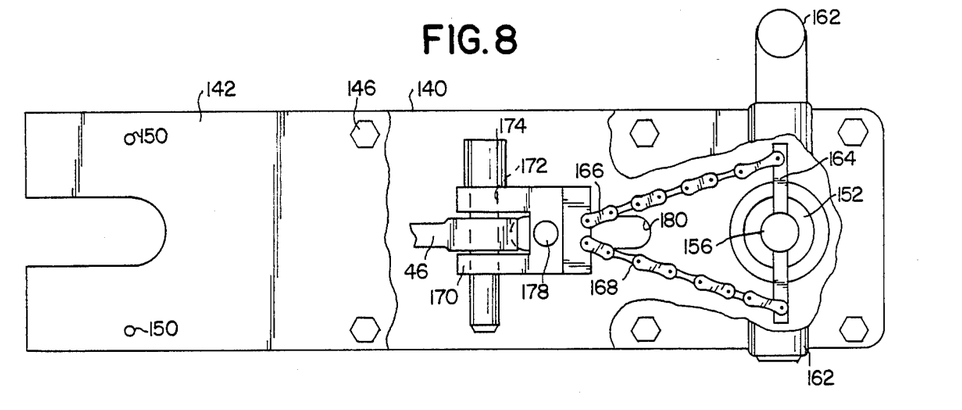
FIG. 8 is a side view of the torque testing attachment.
Figures 9, 10:
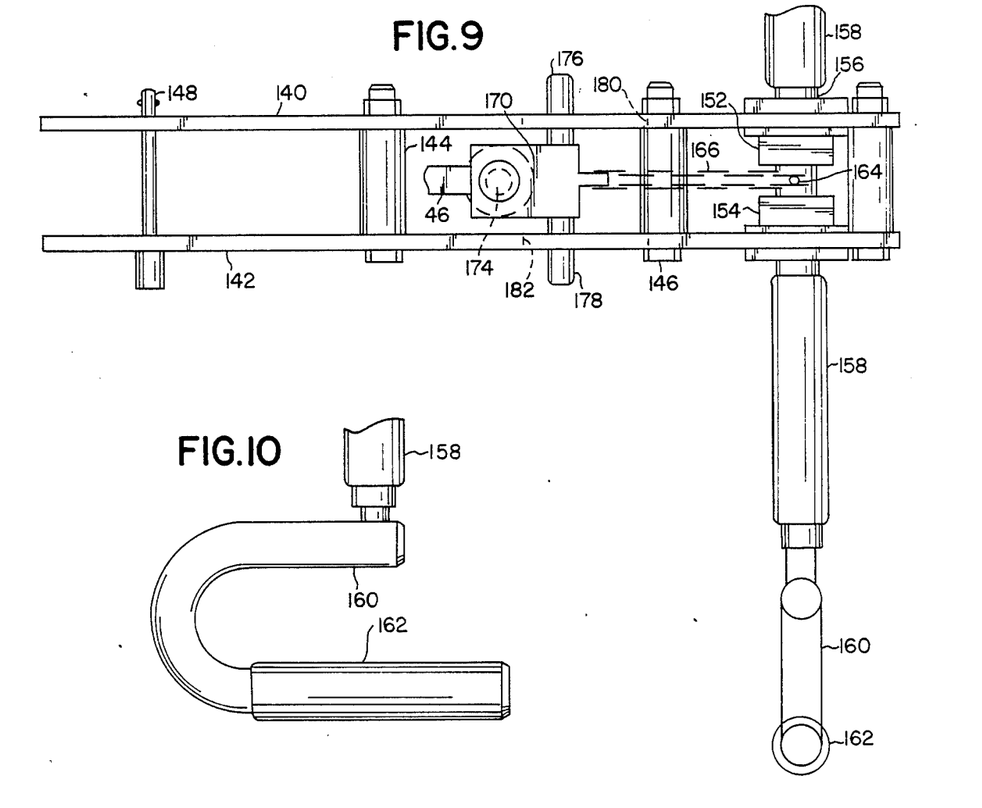
FIG. 9 is a top view of the torque testing attachment.
FIG. 10 is a detail of the torque testing attachment.

In FIGS. 8, 9 and 10 the torque testing unit is illustrated. A pair of side plates 140 and 142 are fastened together with spacers 144 and bolts 146. The side plates attach with a pin 148 through holes 150 in the side plates to the head 40 on the arm 28. At the outboard end of the side plates 140 and 142 are a pair of bearings 152 and 154 mounted in the side plates. A rotatable shaft 156 extends through the bearings 152 and 154 and is covered on each side with grip material 158. Attached to one end of the shaft 156 is a U-shaped rod 160 having a portion covered with grip material 162.

Between the bearings 152 and 154 a lever arm 164 extends above and below the shaft 156 and is attached to the shaft. At the top and bottom of the rod 164 short lengths of chain 166 and 168 are attached. The chains 166 and 168 extend and attach to a bifurcated block 170. The bifurcated block 170 includes a bore 172 through the bifurcated end for a pin 174 attachment to the eye-bolt 46 and load cell 42. Extending horizontally from either side of the block 170 are pins 176 and 178 which engage slots 180 and 182 in the side plates 140 and 142.

Gripping and turning the U-shaped rod 160 provides a test of pronation/supination torque with the forearm parallel to shaft 156. Gripping and turning the U-shaped rod 160 with the forearm perpendicular to the shaft 156 provides a test of ulnar/radial deviation torque. Gripping and turning the shaft 156 provides a test of flexion/extension torque. Thus, all three rotations of the hand can be tested with the torque testing unit at the proper height on the arm 28 and vertical assembly 20. The proper height for the subject person depends upon individual height and desired arm orientation. For example, the subject's arm may be fully extended or the upper arm vertical and lower arm extended.

What is claimed is:

1. A squeeze grip attachment and an isometric strength testing unit, said squeeze grip attachment comprising a frame having two parallel members, an outboard frame bar joining the parallel members, a bifurcated handle positioned between the parallel members, said handle being movable relative to the parallel members, a handle bar extending between the ends of the bifurcated handle, means on the handle engageable with the parallel members and means on the parallel members to guide movement of the handle relative to the frame bar, means on the handle for attachment to a force sensing means in said isometric strength testing unit and means on said parallel members for attachment to said isometric strength testing unit, said 2. The isometric squeeze grip attachment and isometric strength testing unit of claim 1 wherein said guide means and attachment means on the handle are for restricting movement of the handle and handle bar to linear movement relative to the frame bar.

3. The squeeze grip attachment and isometric strength testing unit of claim 1 including means to adjust the unloaded distance between the handle bar and the frame bar.

4. The squeeze grip attachment and isometric strength testing unit of claim 1 wherein the attachment means on the parallel members is adjustable to adjust the unloaded distance between the handle bar and the frame bar.

5. An isometric strength testing unit comprising a vertical post, a horizontal arm on the post, said arm selectably positionable on the post, a squeeze grip attachment on the arm, said squeeze grip attachment comprising a frame having two parallel members, an outboard frame bar joining the parallel members, a bifurcated handle positioned between the parallel members, said handle movable relative to the parallel members, a handle bar extending between the ends of the bifurcated handle, means on the handle engageable with the parallel members and means on the parallel members to guide movement of the handle relative to the frame bar and sensing means attached to the handle.

6. The isometric strength testing unit of claim 3 wherein said guide means and attachment means on the handle are for restricting movement of the handle and handle bar to linear movement relative to the frame bar.

7. The isometric strength testing unit of claim 5 including means to adjust the unloaded distance between the handle bar and the frame bar.

8. The isometric strength testing unit of claim 5 wherein the attachment means on the parallel members is adjustable to adjust the unloaded distance between the handle bar and the frame bar.

9. The isometric strenght testing unit of claim 5 wherein the sensing means includes electrical means to provide an electrical signal in response to a change in handle position relative to the frame bar.

10. A torque testing attachment for an isometric strength testing unit comprising a frame having two parallel spaced apart side members, a transverse shaft having grip means thereon and extending through a pair of bearings, said bearings mounted adjacent the outboard ends of said side members, a lever arm attached to the shaft, non-extendable means attached at one end to the lever arm at a location spaced from the shaft, means for attachment to a sensing means, said non-extendable means being attached at the other end to said sensing means attachment, and means on said side members for attachment to an isometric strength testing unit.

11. The isometric torque testing attachment of claim 10 wherein said grip means comprises a U-shaped member attached to one end of said shaft by one side of the U-shape.

12. The isometric torque testing attachment of claim 10 wherein said lever arm extends on opposite sides of the shaft and a second non-extendable means is attached at one end to the opposite side of the lever arm at a location spaced form the shaft, said second non-extendable means being attached at the other end to said sensing means attachment.

13. The isometric torque testing attachment of claim 10 including guide means in said side members in engagement with the sensing means attachment.

14. An isometric strength testing unit comprising a vertical post, a horizontal arm on the post, said arm selectably positionable on the post, a torque testing attachment on the arm, said torque testing attachment comprising a frame having two parallel spaced apart side members, a transverse shaft having grip means thereon and extending through a pair of bearings, said bearings mounted adjacent the outboard ends of said side members, a lever arm attached to the shaft, non-extendable means attached at one end to the lever arm at a location spaced from the shaft, means for attachment to a sensing means, said non-extendable means being attached at the other end to said sensing means attachment, and means on said side members for attachment to the isometric strength testing unit.

15. The isometric strength testing unit of claim 14 wherein said grip means comprises a U-shaped member attached to one end of said shaft by one side of the U-shape.

16. The isometric strength testing unit of claim 14 wherein said lever arm extends on opposite sides of the shaft and a second non-extendable means is attached at one end to the opposite side of the lever arm at a location spaced from the shaft, said second non-extendable means being attached at the other end to said sensing means attachment.

17. The isometric strength testing unit of claim 14 including guide means in said side members in engagement with the sensing means attachment.

* * * * *

UNITED STATES PATENT AND TRADEMARK OFFICE
CERTIFICATE OF CORRECTION

PATENT NO. : 4,939,933

DATED : July 10, 1990

INVENTOR(S) : Thomas M. Curran

It is certified that error appears in the above-identified patent and that said Letters Patent is hereby corrected as shown below:

Col. 2, line 65: Delete "satistical" and substitute --statistical--.

Col. 4, line 42: Insert --in-- after "modelling".

Col. 4, line 66: Delete "on" and substitute --of--.

Col. 9, line 25: After the end of the line add --isometric strength testing unit comprising vertically positionable means to support said squeeze grip attachment--.

Col. 9, line 26: Delete the first occurance of "isometric".

Col. 9, line 54: Delete "3" and substitute --5--.

Col. 10, line 27: Delete "form" and substitute --from--.

Signed and Sealed this

Third Day of March, 1992

Attest:

HARRY F. MANBECK, JR.

Attesting Officer — Commissioner of Patents and Trademarks

UNITED STATES PATENT AND TRADEMARK OFFICE
CERTIFICATE OF CORRECTION

PATENT NO. : 4,939,933
DATED : July 10, 1990
INVENTOR(S) : Thomas M. Curran

It is certified that error appears in the above-identified patent and that said Letters Patent is hereby corrected as shown below:

In TABLE 1 below Column 6, under "Body Link" in the second, third and fourth subtables reverse the first column of each subtable to read vertically down:

-- Ankle
   Knee
   Hip
   L5/S1
   Shoulder
   Elbow --

Signed and Sealed this

Twentieth Day of April, 1993

Attest:

MICHAEL K. KIRK

*Attesting Officer*     *Acting Commissioner of Patents and Trademarks*